United States Patent [19]

McClelland et al.

[11] Patent Number: 5,075,552
[45] Date of Patent: Dec. 24, 1991

[54] APPARATUS AND METHOD FOR TRANSIENT THERMAL INFRARED EMISSION SPECTROMETRY

[75] Inventors: John F. McClelland; Roger W. Jones, both of Ames, Iowa

[73] Assignee: Iowa State University Research Foundation Inc., Ames, Iowa

[21] Appl. No.: 576,448
[22] PCT Filed: Jan. 12, 1990
[86] PCT No.: PCT/US90/00122
§ 371 Date: Sep. 12, 1990
§ 102(e) Date: Sep. 12, 1990
[87] PCT Pub. No.: WO90/08311
PCT Pub. Date: Jul. 26, 1990

[51] Int. Cl.⁵ .......................................... G01N 21/71
[52] U.S. Cl. .................................. 250/341; 250/339; 250/340
[58] Field of Search .................... 250/341, 340, 339

[56] References Cited

U.S. PATENT DOCUMENTS

| | | | |
|---|---|---|---|
| 3,413,474 | 11/1968 | Freeh | 374/7 |
| 3,631,526 | 12/1971 | Brunton | 250/341 |
| 3,828,173 | 8/1974 | Knepler | 364/498 |
| 4,229,653 | 10/1980 | Uthe | 250/339 |
| 4,337,396 | 6/1982 | Lauer et al. | 250/340 |
| 4,369,886 | 1/1983 | Lane et al. | 209/564 |
| 4,428,902 | 1/1984 | Murray | 376/156 |
| 4,496,839 | 1/1985 | Bernstein et al. | 250/341 |
| 4,564,761 | 1/1986 | Buckwald et al. | 250/341 |
| 4,578,584 | 3/1986 | Baumann et al. | 250/341 |

FOREIGN PATENT DOCUMENTS 2154315  9/1985  United Kingdom ................ 250/339

Primary Examiner—Constantine Hannaher
Attorney, Agent, or Firm—Antonelli, Terry, Stout & Kraus

[57] ABSTRACT

A method and apparatus for enabling analysis of a solid material (16, 42) by applying energy from an energy source (20, 70) top a surface region of the solid material sufficient to cause transient heating in a thin surface layer portion of the solid material (16, 42) so as to enable transient thermal emission of infrared radiation from the thin surface layer portion, and by detecting with a spectrometer/detector (28, 58) substantially only the transient thermal emission of infrared radiation from the thin surface layer portion of the solid material. The detected transient thermal emission of infrared radiation is sufficiently free of self-absorption by the solid material of emitted infrared radiation, so as to be indicative of characteristics relating to molecular composition of the solid material.

34 Claims, 6 Drawing Sheets

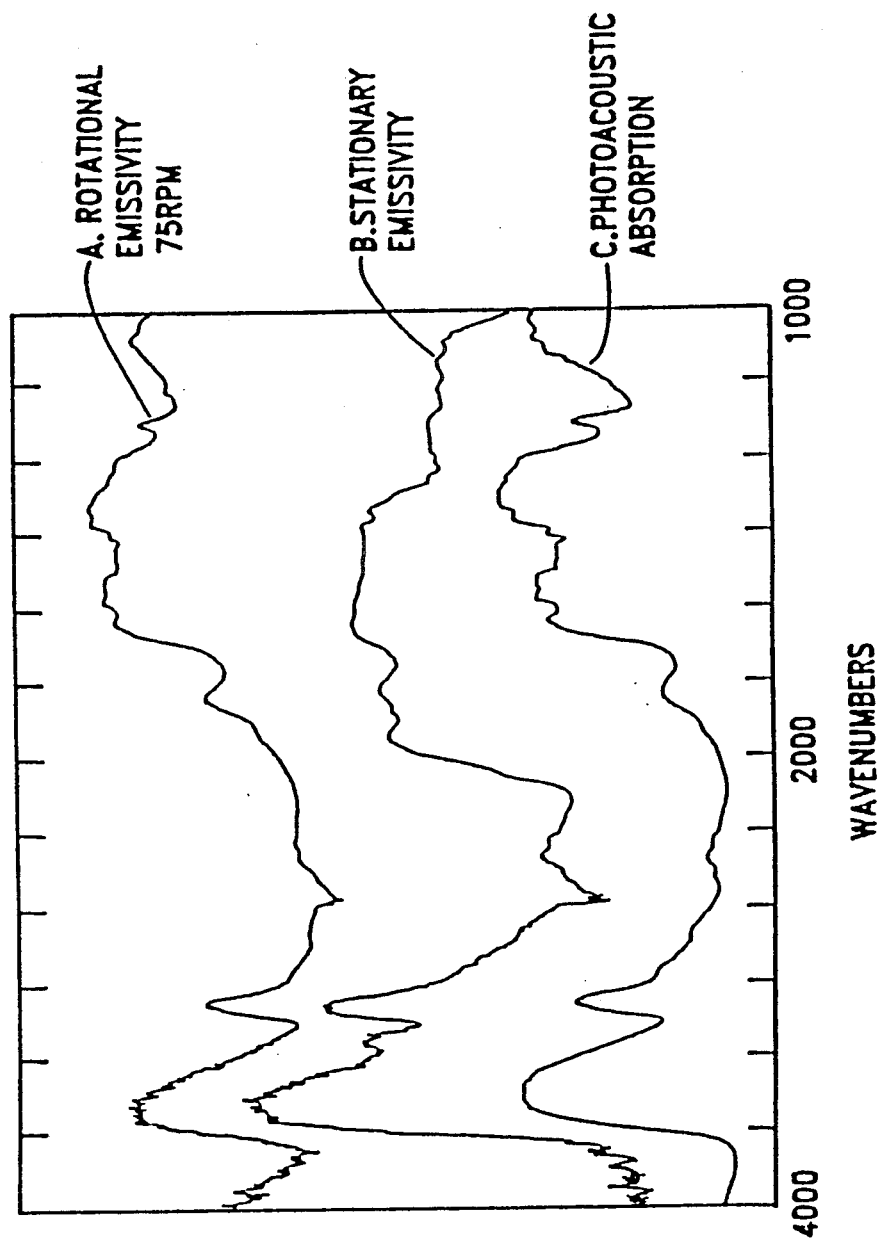

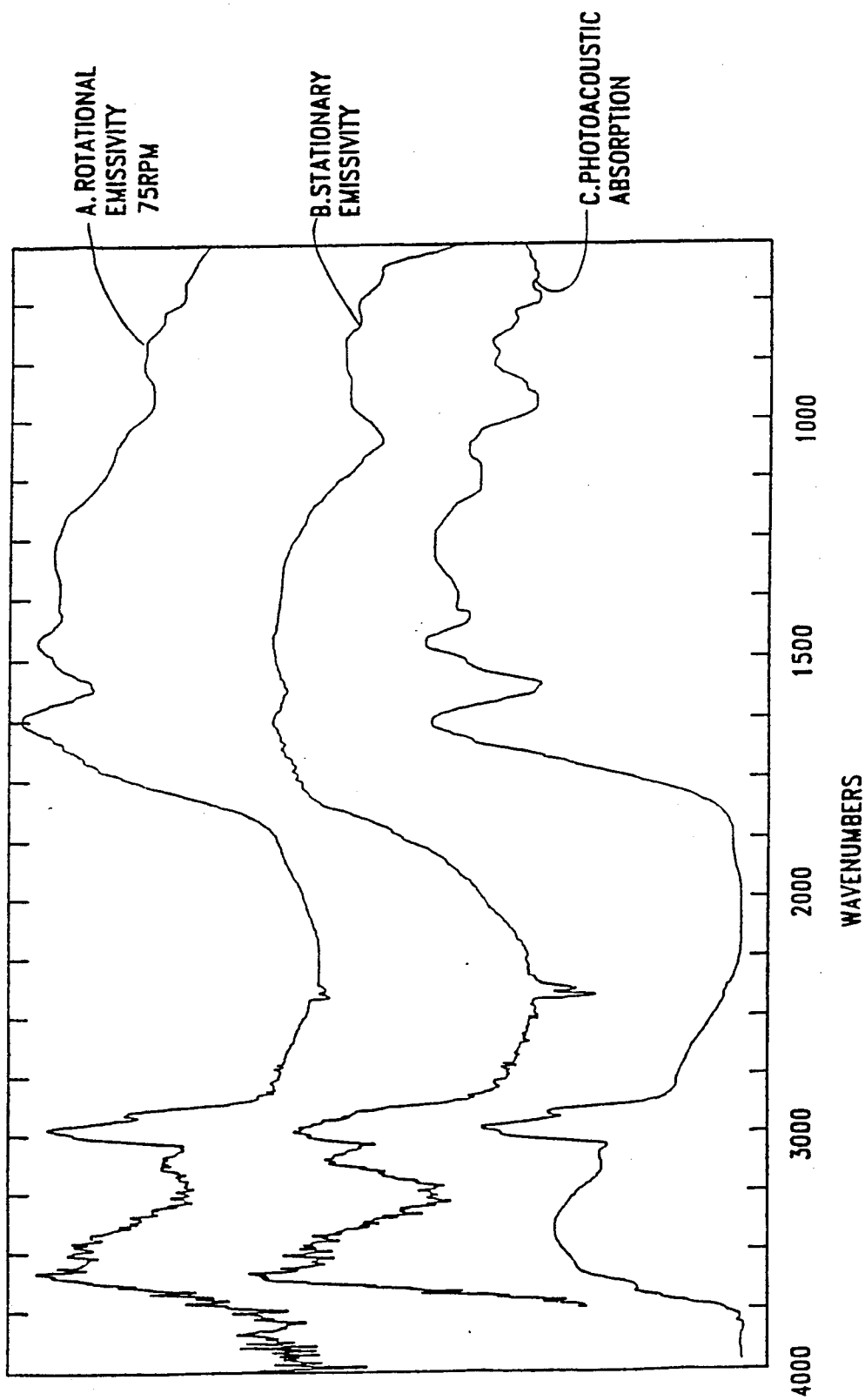

APPARATUS AND METHOD FOR TRANSIENT THERMAL INFRARED EMISSION SPECTROMETRY

TECHNICAL FIELD

The present invention relates to spectroscopic analysis of materials, and particularly, to non-contact, remote spectroscopic analysis of a quantity of moving or stationary material based on transient thermal infrared emission from the material.

BACKGROUND ART

There are numerous types of analytical methods which currently are known for deriving information about materials. Spectroscopy is a well known and general method for analyzing materials. There are a number of types of spectroscopic methods which, in turn, are applicable to certain types of analyses and measurements, and which have advantages and disadvantages.

Presently, there is a need for improvements in the ability to analyze materials, especially in those cases where such analyses need to be quick, efficient, and accurate. Additionally, there is a real need for such analyses for "in-process" situations; that is, directly on-line with respect to the manufacturing or the processing of materials.

Presently, for many materials, there are a variety of generally conventional spectroscopic methods for analyzing the content and other characteristics of the materials. Some of those methods are infrared transmission, diffuse reflectance, photoacoustic, and emission spectroscopies. While generally these methods give satisfactory results, they are deficient because they require selective, and often destructive, sampling of the materials. Some materials (coal, for example) require grinding or pulverizing. The material must often be removed to a remote laboratory location where the testing and equipment requires time and resources to provide the results. Currently, no contemporaneous, non-destructive, on-line infrared analysis is reasonably possible for solid materials including semisolid materials such as flexible or rubber-like materials.

Many of the aforementioned presently used methods also lack much flexibility in their use. While some of the methods do not require destructive sampling such as grinding or pulverizing, they may not be operable for materials of greater than minimal thickness, or for materials of varying thickness. Conventional transmission, reflection, or emission spectroscopies have problems because the optical density of many materials is too high to permit accurate and reliable measurement. That is, upon heating of a sample, such sample strongly reabsorbs the same wavelengths it strongly thermally emits as infrared radiation. When a thick sample is heated, the deep layers of the sample emit strongly at the preferred wavelengths and only weakly at other wavelengths. This deep-layer strong emission at preferred wavelengths, however, is greatly attenuated before leaving the sample since surface layers of the thick sample preferentially abosrb those particular wavelengths and such process is termed "self-absorption". Self-absorption in optically-thick samples causes severe truncation of strong spectroscopic bands and leads to emission spectra which closely resemble black-body emission spectra representative of an optically thick material being heated to a uniform temperature and which contain little spectral structure characteristic of the material being analyzed.

Attempts have been made to solve this self-absorption problem by thinning sample materials. High-quality spectra of free-standing films and thin layers on low-emission substrates are routinely measured. However, this requires selective sampling and processing of the materials being analyzed.

For other types of spectroscopic methods such as photoacoustic spectrometry which are less subject to optical density problems, deficiencies exist in that they are not easily performed on moving streams of solid materials. Thus, there is a real need in the art for an apparatus and method which has the flexibility to be used both for moving and stationary materials; and for materials which may have significant optical densities.

There is a further need for an apparatus and method which does not require the use of additive materials to or processing of the sample materials, and which can analyze non-destructively and remotely. For example, in some spectroscopic methods, the materials must be ground to fine powders and then diluted in a transparent matrix. Of course, any destructive processing or additive procedures would alter the beginning state of the material being analyzed. For an analytical apparatus and method to be used effectively in a production line, any fundamental change in the material must be avoided. For example, if variable-in-size crushed coal were being analyzed on a moving conveyor, no grinding or addition of any substance would be allowed, as the coal could not then be utilized for its intended purpose in its original state.

DISCLOSURE OF THE INVENTION

It is therefore a principal object of the present invention to improve upon or overcome the deficiencies and problems in the art.

Another object of the present invention is to provide an apparatus and method of thermal transient infrared emission spectroscopy which can be utilized on either moving or stationary materials.

Another object to the present invention is to provide an apparatus and method as above described which can be accomplished generally without physical contact with the material.

A further object to the present invention is to provide an apparatus and method as above described which can be done remotely from the material being analyzed.

A further object to the present invention is to provide an apparatus and method as above described which can derive the molecular composition of a material, and various physical and chemical properties of the material that are related to molecular composition.

Another object to the present invention is to provide an apparatus and method as above described which can be utilized directly on production or processing lines which handle the materials.

A still further object to the present invention is to provide an apparatus and method as above described which is non-destructive to the material being analyzed.

A further object to the present invention is to provide an apparatus and method as above described which can also be utilized to analyze either large or small samples of the materials in laboratory settings.

A still further object to the present invention is to provide an apparatus and method as above described which can be utilized with optically dense materials.

A further object to the present invention is to provide an apparatus and method as above described which overcomes the spectroscopic problems caused by self-absorption of the emitted radiation from the material being analyzed.

A further object of the present invention is to provide an apparatus and method as above described which can be utilized for stationary materials, or for an unknown quantity of moving material, on both a continuous and non-destructive basis.

Another object of the present invention is to provide an apparatus and method as above described which can be directly utilized in-process for an unknown quantity of moving material.

A further object of the present invention is to provide an apparatus and method as above described which is economical, efficient and reliable.

Another object of the present invention is to provide an apparatus and method as above described which can operate within the extreme and changing conditions of a processing environment for materials, or within a laboratory setting.

A further object of the invention is to provide an apparatus and method as above described, which can be combined with a computer system to derive information about the materials useful for processing, control, and understanding of the material.

The present invention provides an apparatus and method for nondestructively analyzing either stationary or moving materials, particularly solid materials, by infrared spectroscopy. Energy is applied to a surface region of the material so as to cause transient heating in a thin surface layer portion of the material and enable transient thermal emission of infrared radiation from the thin surface layer portion. That is, a fraction of the energy is absorbed near the surface, heats a thin, near surface layer of the material, and causes thermal emission of infrared radiation. Substantially only the transient thermal emission of infrared radiation from the thin surface layer portion which is substantially free of self-absorption, is detected as an infrared spectrum by a spectrometer, for example. The spectrum contains information on the molecular composition of the material. Thereafter characteristics relating to the molecular composition of the material may be determined based upon the detected transient thermal infrared emission.

In accordance with the present invention, the energy source supplies sufficient energy to the surface of the material to cause transient heating in the surface layer portion and may be a pulsed energy source such as a pulsed laser, electron, or ion beam, or other pulsed energy source. Alternatively, transient heating of the surface layer portion can also be created by utilizing a continuous energy beam directed at a moving material with the energy beams also being moved or oscillated, if desired. For example, in accordance with a feature of the present invention, a thermal energy source such as a hot gas jet is utilized to create transient heating in the material. Further, a heated roller or the like, may be utilized to contact the surface of the material so as to cause transient heating. Also, a strongly absorbed energy source, such as a laser, may be used to cause the transient heating and thermal infrared emission. Additionally, other energy sources can be utilized to create transient heating within the material such as electron or ion generators, operating in either continuous or pulse modes, hot gas jets, and heated rollers, as well as others.

In accordance with the present invention, the analysis and detection of the thermal infrared emission is accomplished by a spectrometer and detector which, in preferred embodiments, can be, for example, an optical filter spectrometer, a Fourier transform infrared spectrometer (FTIR) or a cooled HgCdTe infrared detector. The detector operates so as to detect substantially only the transient thermal emission of infrared radiation from the thin surface layer portion which is substantially free of self-absorption by the material of emitted infrared radiation. Such detection may be achieved in the case of a pulsed energy source applied to a stationary material by controlling the operation of the detector in accordance with the application of the pulsed energy so that the detector is activated for a predetermined period. That is, a period of time after the transient thermal emission of the infrared radiation from the thin surface layer portion, the self-absorption by the material of emitted infrared radiation results in essentially black-body emission spectra to be detected which black-body emission spectra prevents a determination of characteristics relating to the molecular composition of the material. Accordingly, the operation of the detector is controlled to detect the desired transient thermal emission and exclude other emissions as by gating of the detector in synchronization with the pulsed energy application to the surface of the material. Alternatively, if a continuous energy beam is applied to the surface of the material and the material is moving, the field of view of the detector is set in relation to movement of the material so that substantially only the transient thermal emission of the infrared radiation from the surface layer portion appears within the field of view of the detector as a result of movement of the material. Control arrangements may also be provided so as to be able to detect the transient thermal emission of the infrared radiation from the surface layer portion by suitable processing of the detected spectra. That is, by suitable filtering of the detected wavelengths, it is possible that the wavelengths of the applied energy source are present within the field of view of the detector and filtered out so that the transient thermal infrared emission is appropriately detected and recognized.

In accordance with the present invention, the detector may be controlled by a control arrangement and/or provide an output to a control arrangement including a processor having appropriate software for deriving different characteristics from the detected and selected spectra of the infrared radiation from the material. Additionally, such control arrangement or processor may include appropriate computer memory, storage, and printer or graphic components.

The invention can be utilized as a non-contact, remote analytical apparatus and method for measuring infrared absorbance spectra of materials, either in a moving stream or in a stationary setting. The heating of the thin, near surface layer of the material can be accomplished by either pulsing energy in time onto the material, or moving the material relative to the energy, or both. Thermal infrared emission from the thin layer is analyzed by the detector to obtain infrared absorbance spectra of the material utilizing Kirchhoff's law. The infrared absorbance spectra are then used to determine molecular composition and other correlated properties.

The invention therefore provides efficient and accurate emission spectroscopic analysis of materials. It eliminates the selective sampling, grinding or other preparation required by presently utilized systems.

The invention can also be adapted to a variety of situations. It can be utilized in laboratory settings for a variety of different types and sizes of materials, and it can be utilized on-line in production settings. By utilizing computer software and hardware, it can form an integral part of process control by being able to derive this information during processing, without contact or sampling, or destruction of the material being processed. It can also be used to assist in controlling how the processing of the material proceeds.

These and other objects, features, and advantages of the present invention will become more apparent with reference to the accompanying drawings.

BRIEF DESCRIPTION OF THE DRAWINGS

FIG. 3 is a graphical depiction of observed emissivity spectra for a phenolic-plastic disk sample. Results utilizing the invention with the sample rotating, and stationary, are compared to a reference photoacoustic absorption spectrum of phenolic-plastic.

FIG. 4 is similar to FIG. 3, except it graphically depicts emissivity spectra of a coal sample.

BEST MODE FOR CARRYING OUT THE INVENTION

With respect to the drawings, a detailed description of the preferred embodiments of the invention will now be described. This description is by way of example only and is not intended to limit the scope or applications of the invention.

Figure 1:
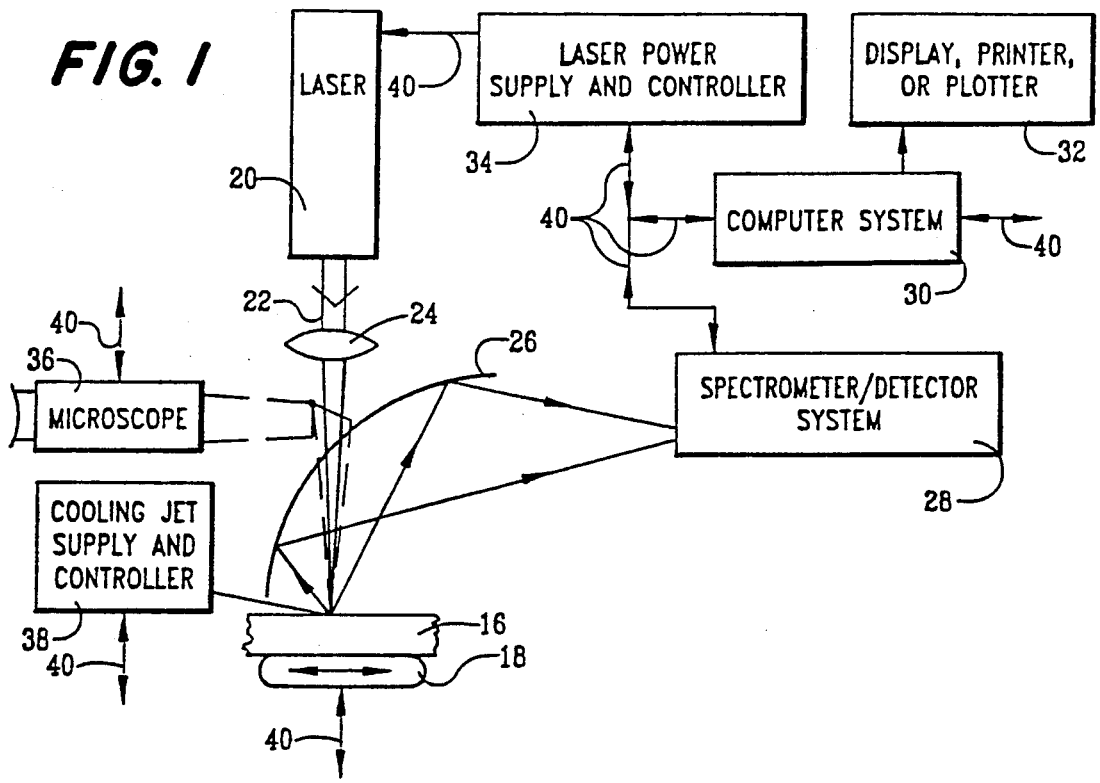
FIG. 1 is a schematic depiction of an embodiment of the invention.

A preferred embodiment of the invention is shown at FIG. 1. The embodiment of FIG. 1 can be used to analyze either stationary or moving materials.

By referring to FIG. 1, it can be seen that in this embodiment the sample or material to be analyzed is designated by reference numeral 16. A sample position controller 18 can comprise either a material transporter such as a conveyor or some other type of positioner. For example, controller 18 could be a rotary table. Still further, controller 18 could simply be a positioning table (for example an X-Y-Z positioning table) which can be controlled to accurately position a stationary sample material. The type of sample position controller 18 used depends upon the selected operation of the invention.

The energy source in FIG. 1 consists of a laser 20 which can be operated either in a pulsed or CW (continuous wave) mode. Laser beam 22 from laser 20 would be directed towards material 16. Focusing optics 24 would serve to pinpoint the laser beam 22 onto material 16. Collection optics 26, such as are known in the art, are used to focus infrared radiation emitted by sample material 16 onto spectrometer/detector system 28. System 28 generates an electrical signal as a function of the wave number of the emitted radiation.

The embodiment of FIG. 1 also includes computer system 30 which controls the spectrometer/detector system 28 as well as controller 18, 34 and 38 and processes the spectrometer/detector system 28 signals in order to obtain the chemical or physical information required from the analysis. The computer system 30 also controls measurement components, displays results, and commands auxiliary systems. Reference numeral 32 refers generally to a computer display, printer, and/or plotter.

Laser 20 is powered by a laser power supply in controller 34. Moreover, in the embodiment in FIG. 1, there is shown a microscope system 36 having appropriate optics for viewing the analysis area on sample material 16; that is, the area of intersection of focused laser beam 22 onto material 16. Additionally, a cooling jet supply and controller 38 can be operatively associated with the embodiment of FIG. 1 to be able to supply a cooling jet of gas to the general area of inter-section of laser beam 22 with material 16.

Reference numeral 40 designates communication connections or links between computer system 30 and other components and controls of the embodiment. Computer system 30 can therefore, by appropriate software, operate laser power supply controller 34, sample position controller 18, spectrometer/detector system 28, microscope system 36, and cooling jet supply and controller 38. Other components and controls can also optionally be operated by computer system 30, according to desire.

The embodiment of FIG. 1 is flexible and adaptable to be used for different materials, and different analytical procedures. This embodiment can analyze moving or stationary solid materials. It imposes a surface absorbed energy beam upon material 16 causing transient heating in a thin surface layer of material 16 by pulsing the energy beam over time, or by rapid relative motion between the beam 22 and material 16; or by a combination of both. The transient thin layer heating causes emission of infrared radiation from a shallow enough depth to be sufficiently free of self-absorption to allow an infrared spectrum of material 16 to be measured. The emitted radiation from the thin layer is detected and measured by spectrometer/detector system 28. Computer system 30 then processes the signal to obtain molecular concentrations or other physical or chemical information through correlation techniques as required for any number of different operations, such as a process control, quality control, analytical chemistry, or non-destructive evaluation applications.

Laser 20 can be a UV laser (a strongly absorbed pulsed energy source). Spectrometer/detector system 28 can be one or more optical filter spectrometers with infrared detectors, a Fourier transform infrared (FTIR) spectrometer, or other spectrometers with an infrared detector such as an ambient temperature infrared detector or a HgCdTe or high $T_c$ superconducting detector operating at liquid nitrogen temperature.

Computer system 30 can include appropriate computer software and complementary data for deriving different material characteristics from infrared emission spectra. Additionally, it can use appropriate software, displays, complementary data and servo systems to make decisions and send and execute commands based on the infrared spectra.

Operation of the embodiment of FIG. 1 can first be described with regard to a sample 16 which is in motion with respect to laser beam 22. In this case, laser 22 is focused by optics 24 on sample 16, which for example, could be coal moving on a conveyor belt, or coal attached to a rotating disc, such as is generally indicated at reference numeral 18. The relative motion between the laser beam 22 and sample 16 produces a transient heating effect in a thin surface layer of the sample which is sweeping past the focal spot of the laser beam 22. It is to be understood that a similar transient may be generated by pulsing the intensity of the laser beam as a function of time if sample 16 were stationary.

The maximum layer thickness observed by spectrometer/detector 28 for the moving sample 16 can be estimated by $(4Dr/v)^{\frac{1}{2}}$ where D is thermal diffusivity of sample 16, r is the object diameter from which emitted radiation is focused into the spectrometer/detector 28, and v is the sample velocity. In comparison, in the case where laser 20 is pulsed and sample 16 is stationary, the maximum layer thickness expression is $(4D\tau)^{\frac{1}{2}}$ where $\tau$ is the laser repetition period. It is also to be understood that depending on the application, it may also be desirable to both move the sample and pulse the beam. If long term temperature build-up occurs in the sample, cooling jet supply 38 can be employed to remedy this situation.

Radiation emitted by the thin heated layer is focused by collection optics 26 on the infrared spectrometer detector system 28. System 28 and computer system 30 measure the emitted radiation intensity as a function of wave number in terms of an electrical signal. The computer output peripherals (display, printer, and/or plotter 32) display and record data. The computer 30 processes the infrared data to determine various material properties. The computer 30 uses communication or command links 40 to control various components of the measurement system, for example the laser power supply 34; and to control other systems, such as processing equipment (not shown) based on material properties determined by the on-line measurements.

The embodiment of FIG. 1 can also be utilized on a stationary sample 16. The stationary measurement mode is appropriate for use in analytical laboratories where a moving stream of material is not present. In this case, laser 20 is pulsed with a pulse time which is short on the scale of the pulse repetition time. Furthermore, cooling jet 38 is employed to prevent the long term build-up of heat in the sample 16. Microscope viewing system 36 can be employed to position the focal spot of the laser 20 at a precise location on the sample 16. This allows for microanalysis. In other regards the stationary sample measurement mode is similar to the moving sample embodiment described above.

In the case of a pulsed laser 20 and a stationary or rotating sample 16, due to the pulsed nature of the transient thermal emission from the thin surface layer portion produced by the laser irradiation, it is preferable to synchronize the laser firing with the spectrometer/detector system 23 sampling under control of the computer system 30. The spectrometer/detector system may include a detector preamplifier and an A/D converter and by inserting a gated integrator between the output of the detector preamplifier and the A/D converter, a pulse utilized to trigger the A/D converter and the integrator may also be utilized to fire the laser and control sampling by way of the computer system 30. In this manner the detection by the spectrometer/detector is gated in accordance with the firing of the laser to detect the transient thermal emission of infrared emission from the thin surface layer of the material for a short time period after each laser pulse thereby avoiding detection of emissions affected by self-absorption. Alternatively, a continuous laser whose beam is chopped may be utilized with a detector system having a lock-in amplifier so that selective measurement of a signal occurring at the chopping frequency is effected. The use of a lock-in amplifier may also produce a less noisy signal since it eliminates most noise at all frequencies other than the one it monitors. Additionally, if the chopping frequency is much higher that the sampling rate of the A/D converter in the spectrometer/detector, synchronization of the chopping and the spectrometer/detector may not be necessary. Also, it is possible to effect relative movement of the energy beam and the field of view of the spectrometer/detector with respect to the surface of the sample material independent of sample material velocity. For example, by providing an oscillating mirror in the energy beam path and the field of view of spectrometer/detector with a linear moving sample material, the energy beam and field of view are moved by oscillation of the mirror perpendicular to the direction of sample material motion and such results in a zig-zag track for the beam and field of view. Furthermore, the spectrometer/detector can be provided with suitable filters so that even though the energy beam is within the field of view, the wavelength thereof is filtered out.

Figure 1A:
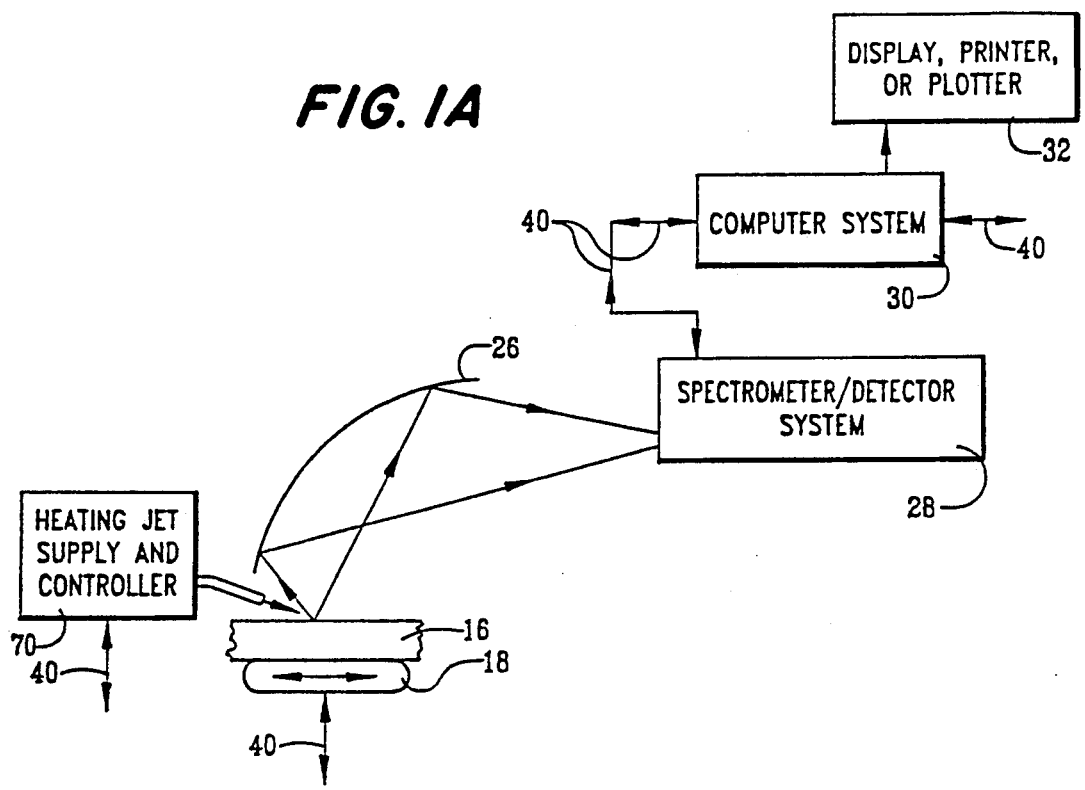
FIG. 1a is similar to FIG. 1 except it utilizes an alternative heating source to the laser of FIG. 1.

FIG. 1a is essentially the same as FIG. 1 except that a heating jet supply and controller 70 is utilized to impose heat energy upon sample 16, instead of laser 20 of FIG. 1. Heating jet supply and controller 70 is configured to impose a jet of heated gas onto material 16 to produce transient heating in the surface of material 16. As with FIG. 1, the remaining components serve to collect the infrared radiation and process the same.

It is to be noted that heating jet supply and controller 70 is operatively connected to computer system 30 and can be controlled accordingly.

Heating jet supply and controller 70 produces a hot gas heating jet which can be imposed on sample 16 to generate transient heating. This embodiment is especially useful for materials that are not strongly absorbing of energy sources such as lasers. It is also economical and non-complex.

This alternative method of generating transient heat in material 16 highlights the fact that a number of different sources can be utilized to create such transient heating for purposes of the invention. As previously mentioned, other energy beams such as electron and ion beams can be utilized, both either in a continuous or a pulsed mode. Further, a heated roller or the like may be utilized to contact the surface of the material so as to enable transient heating. The type of heating source can be selected according to desire and depends upon a number of factors specific to each situation. These factors include but are not limited to the characteristics and parameters of various energy sources, as well as the type of material being analyzed.

Figure 2:
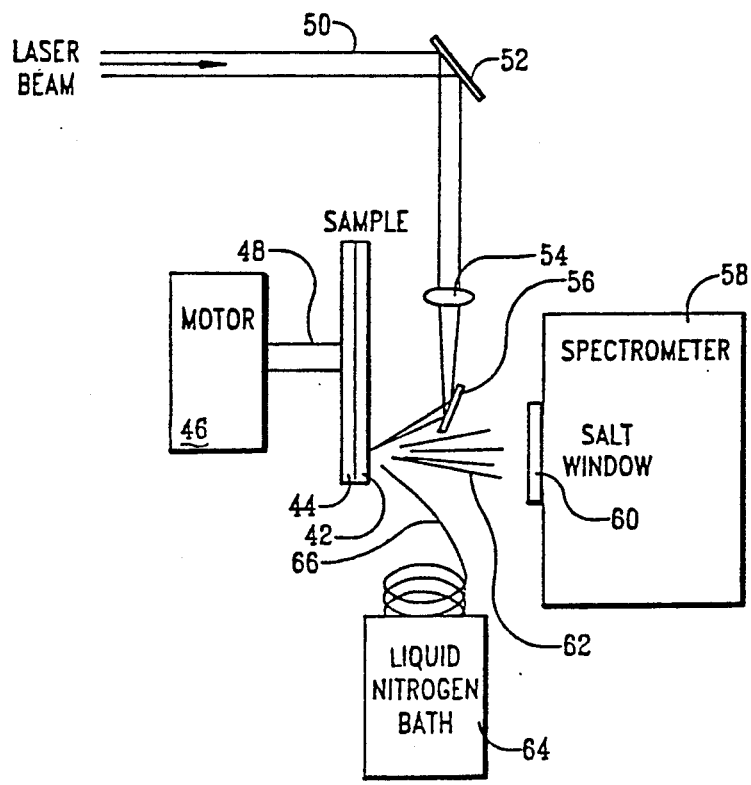
FIG. 2 is a schematic depiction of a further embodiment of the invention.

FIG. 2 shows another embodiment of the present invention for a better understanding of the invention. This embodiment was used to generate the spectra illustrated in FIGS. 3 through 6. A sample material 42 is contained on and secured to a rotating disk 44. A motor 46 has an axle 48 which spins disk 44.

A fixed CW laser beam 50 is directed to a mirror 52 which in turn directs beam 50 through focusing optics 54, which can comprise a focusing lens. Another mirror 56 is adjustable to direct beam 50 to a desired location on disk 44.

For the purpose of recording the spectra in FIGS. 3 through 6, disk 44 was either made of or covered with the sample material 42 and mounted on the axle 48 of variable-speed motor 46, and placed at the normal source position of a Perkin-Elmer 1800 Fourier Transform Spectrophotometer 58. Beam 50, from an argon-ion laser operating in the multi-line mode at up to 3.5 W, was focused on the disk 44 at a 45° angle to a spot approximately 0.8 mm in diameter positioned 3.9 cm from the center of the disk 44. The spectrometer 58 observed the sample 42, normal to the sample surface with the laser focus centered in the spectrometer's 8 mm diameter field of view. The entry port of the spectrometer 58 was 5 cm from the disk 44 and was covered with a salt window 60. No special additional optics were used to better match the small source size to the 8 mm wide field of view. The spectrometer 58 was fitted with a wide-band liquid nitrogen-cooled HgCdTe detector ($D^* = 1 \times 10^{10}$ cm Hz$^{\frac{1}{2}}$/W) and accumulate 256 scans in single-beam mode with a 1.50 cm/s optical-path-difference velocity and 4 cm$^{-1}$ nominal resolution.

In some cases, a sample cooling jet 64 of chilled helium gas was used. A coil 66 of 1.6 mm diameter stainless-steel tubing carrying helium was immersed in liquid nitrogen. The open end of the tubing 66 directed the jet onto the disk 44 0.5 cm from the laser focus so that the rotation of the disk 44 carried the area irradiated by the laser 50 into the jet 64 immediately after such area left the spectrometer 58 field of view.

It can therefore be seen that the embodiment of FIG. 2 shows, in detail, another configuration for practicing the present invention. By using a laser beam or other energy source that will be absorbed very near the surface of the sample material 42, the invention provides that only a thin surface layer is directly heated. In this embodiment, utilizing the rotating disk 44, the layer is transient since thermal diffusion will cause the heated layer to thicken and cool rapidly.

On the other hand, for comparison, if a pulsed laser is used on a stationary sample, the layer is present in the sample at the position of the laser beam for a short time immediately following the laser pulse. It is to be understood that if a continuous laser is used, it must be either scanned across the sample surface, which would require a scanning apparatus, or the sample must be translated through the beam path. The transient layer then exists in the beam track across the sample at and immediately behind the beam position.

Figure 2A:
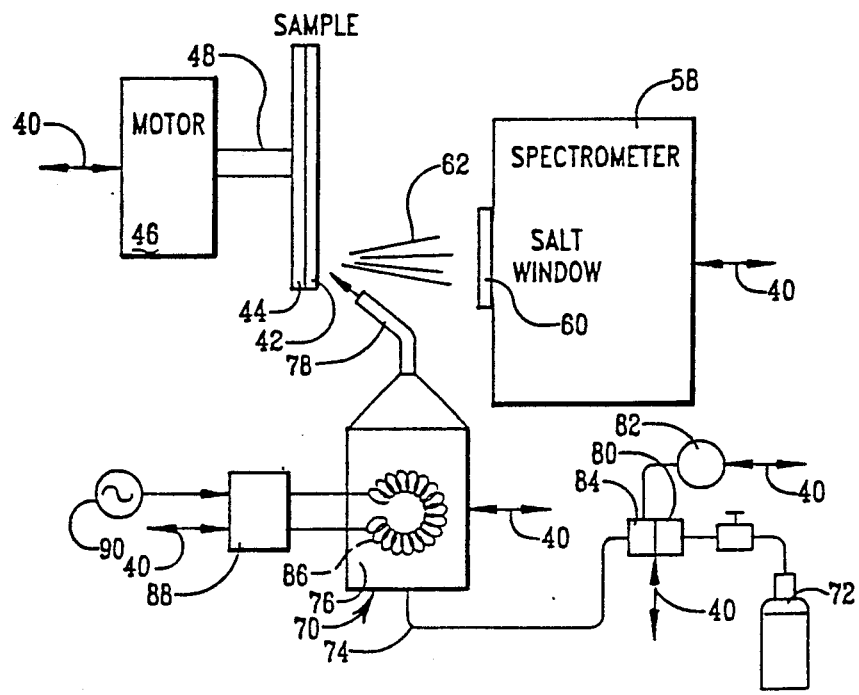
FIG. 2a is a schematic depiction similar to FIG. 2 except it utilizes a different heating source than the laser of FIG. 2.

FIG. 2a depicts essentially the same embodiment as FIG. 2, except that instead of utilizing a laser beam 50 to produce heating on sample 42, a heating jet supply and controller 70, such as discussed with respect to FIG. 1a, could be utilized. This embodiment, utilizing the rotating sample, could readily be adapted to position the hot gas jet upon a portion of sample 42 as it rotates by. This would create the transient heating which would produce the transient thermal emission of infrared radiation from the thin surface layer of the sample material which would be detected by spectrometer 56.

FIG. 2a schematically depicts one configuration for heating jet supply and controller 70. It is to be understood that this is but one configuration, and others can be used while staying within the scope of the invention. For example, it is possible to in effect pulse the temperature of the gas jet by rapidly switching between a hot and a cold flow through the nozzle. Alternatively, the jet can be scanned or oscillated in a direction perpendicular to the sample motion by providing a jet in the form of a series of nozzles along a rim of a rotating wheel which nozzles apply the gas jet to the sample. The spectrometer/detector would then sample the emission from the sample material as each jet passed through its field of view. Here again, it is possible to alternate hot and cold jets from the series of nozzles.

In accordance with FIG. 2a, to supply the jet of heated gas to the sample, the pressurized gas canister 72 is operatively connected by hose 74 to heating chamber 76. The pressurized gas is heated in heating chamber 76 and channeled into jet nozzle 78, which is positioned to direct the gas jet onto the sample 42. In this configuration, gas canister 72, such as is well known in the art, has an on/off valve, and can also have a regulator 80, a flow meter 82, and an electrical valve 84 connected in line to gas canister 72.

Heating of the gas in heating chamber 76 can be accomplished by positioning an electrical resistance heating element 86, such as is well known in the art, within heating chamber 76. Heating element 86 would in turn be operatively connected to a variable transformer 88, which can be electrically controlled to adjust the current through heating element 86, to in turn control how much heat is generated. Transformer 88 would also be operatively connected to an electrical power source 90.

In the configuration shown in FIG. 2a, compressed nitrogen gas is utilized, but it is to be understood that other gases, including air, could also be used. Still further, other methods of heating the gas are possible. This same configuration could be used for heating jet supply and controller 70 in FIG. 1a.

It is to be understood, as indicated in FIG. 2a by reference numerals 40, that each of the motor 46, spectrometer 58, electrical flow valve 84, variable transformer 88, and flow meter 82 could be operatively connected to a system controller such as a computer.

With respect to all of the embodiments described, once the thin heated surface layer is created, the emission from it is analyzed by an FTIR or other infrared spectrometer to obtain an emission spectrum which can be converted by spectrum analysis, according to Kirchhoff's Law, to an absorbance spectrum. Spectral information obtained from the invention, therefore, is similar to that yielded by other types of infrared measurements (transmission, photoacoustic, or diffuse reflectance). Like infrared absorption, the invention is able to determine nondestructively not only molecular properties, but also many other material properties that are related to molecular structure. Such determinations can be made with the aid of existing software which correlates properties with infrared spectral structure. Spectra from the invention of heterogeneous samples can be expected to have some band intensity differences relative to spectra of the other measurement techniques due to differences in the heating efficiency of the excitation beam for different components. This effect can be compensated for in the data treatment.

It is to be understood, that intensities of observed emission spectra may fall off with increasing wavenumber in the same manner as black-body emission curves. Additionally, sources other than the sample 42 (such as the spectrometer 58 itself) may contribute a background emission. These may be corrected for by converting the emission spectra to emissivity spectra. According to Kirchhoff's Law, emissivity is proportional to the fraction of light absorbed when it strikes the surface of a body and so an emissivity spectrum is analogous to an absorbance spectrum. Although Kirchhoff's Law strictly applies only at thermal equilibrium, emissivity spectra based on the emission spectra of the invention closely resemble absorbance spectra. An emissivity spectrum $\epsilon$ may be calculated from an emission spectrum using the equation $\epsilon = (S_1 - S_2)/(B_1 - B_2)$, where S and B are the observed sample and black-body emission spectra and the subscripts refer to two temperatures, $T_1$ and $T_2$, $T_1$ is an effective elevated temperature which is induced by the transient laser heating and $T_2$ is ambient. $S_2$ and $B_2$ correct for background emission while the division by B compensates for the Planck black-body modulation and for the response curve of the spectrometer and detector. In practice, $S_2$, $B_1$ and $B_2$ are determined by complementary measurements. A comparison of emissivity derived from the present invention and photoacoustic absorbance spectra of a variety of samples has shown that emissivity spectra of the invention are nearly identical to absorbance spectra as predicted by Kirchhoff's Law. Comparisons of the results of the invention were made with infrared absorption spectra recorded using photoacoustic detection. These results are shown in FIGS. 3–6. An MTEC Model 200 Photoacoustic Cell was mounted in the FTIR spectrophotometer (with the spectrophotometer's normal light source) and 32 scans were accumulated at 0.05 cm/s optical-path-difference velocity and 8 cm$^{-1}$ nominal resolution. The times required to record a reference photoacoustic spectrum and a spectrum according to the invention were both about three minutes. It is understood that the determination of molecular properties and other material properties related to molecular properties does not require conversion of observed emission spectra to emissivity spectra as described above. Such conversion is only necessary to produce spectra analogous to absorbance spectra.

FIGS. 3–6 depict emissivity spectra for phenolic plastic, coal, blue-green paint, and electrical tape respectively.

In FIG. 3, emissivity spectra (curves A and B) are shown for a smooth-surfaced, 3.0 mm thick, red-colored, filled-phenolic-plastic (Synthane brand) disk and compared to a reference absorption spectrum (C) obtained photoacoustically. Curve A represents an emissivity curve for a rotating sample at 75 revolutions per minute (rpm) with the spectrometer observing the transient thermal emission from the thin, heated layer as detailed in the above embodiment description. Curve B, by contrast, is the emissivity curve produced by the same sample when stationary. With a stationary sample, no transient emitting layer exists since the bulk of the sample is heated by the laser beam, and so the resulting emissivity curve is very similar to that observed by traditional emission spectroscopy. The superiority of Curve A over Curve B (that is, the greater similarity of Curve A to the reference spectrum, Curve C) is the direct result of the method of this invention.

Coal was used as a second example of the improvements attained by observing transient rather than steady-state emission (see FIG. 4). Because of the roughness of the coal, its surface varied in and out from the spectrometer entry port by about 2 mm when the disk was rotating. This roughness caused fluctuations in the signal intensity observed by the spectrometer, but did not appreciably increase the noise in the resulting spectrum. Again, curve A relates to emissivity based on the coal sample being rotated at 75 rpm, and curve B relates to emissivity from a stationary sample. Curve C again is a reference curve based on photoacoustic absorption measurements of coal, and again Curve A is more similar to Curve C than Curve B is.

Figure 5:
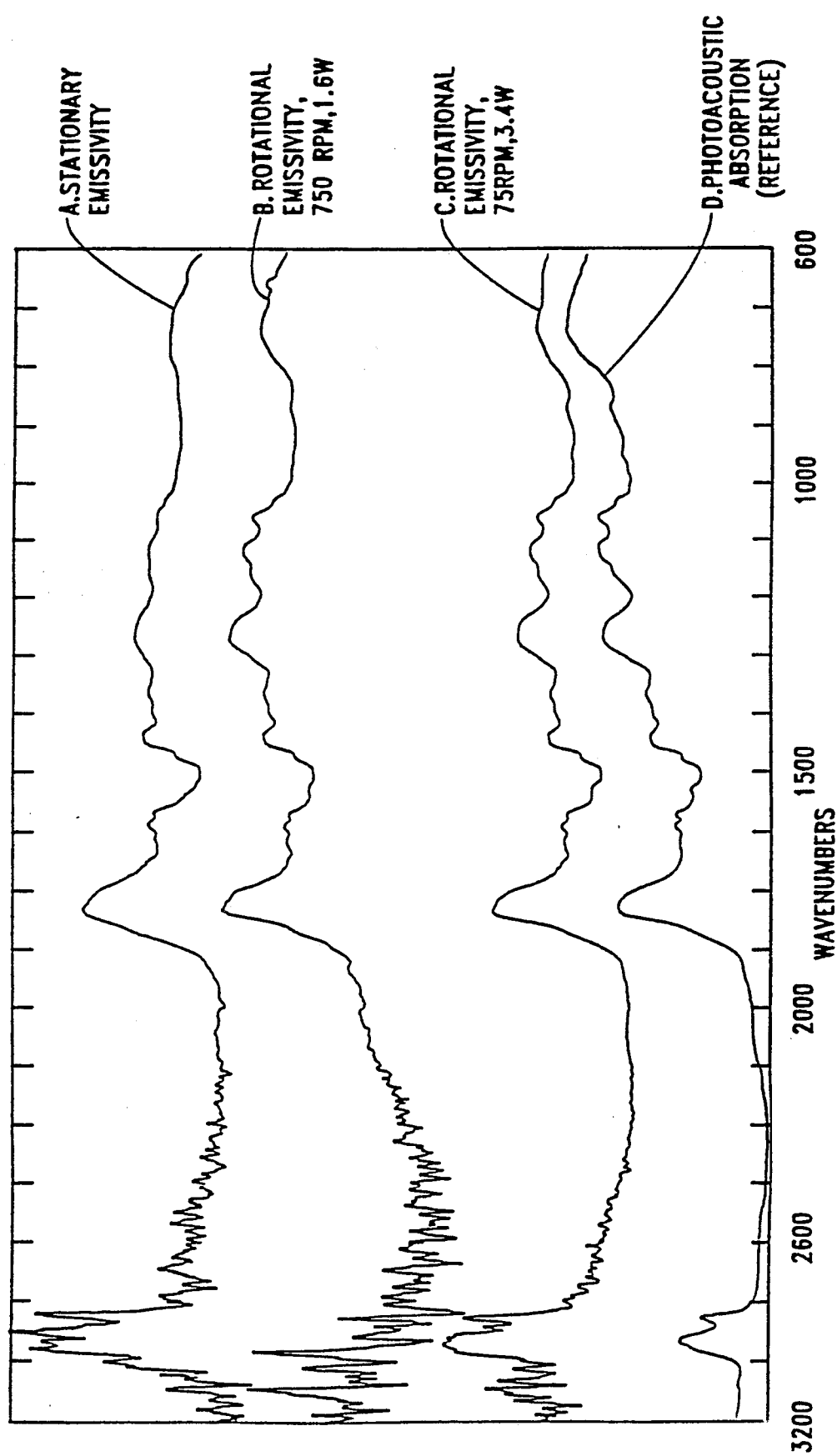
FIG. 5 is similar to FIGS. 3 and 4 except it graphically depicts emissivity spectra of blue-green paint on aluminum, and shows spectra of both a stationary sample, and a sample rotating at two different speeds, compared to a reference photoacoustic absorption spectrum of the paint.

FIG. 5 depicts emissivity curves measured according to the present invention with respect to a 3 mm thick aluminum plate coated with blue-green baked-enamel paint. The paint tested how well the invention could handle a low-signal sample and a very thin sample. The low signal results both because the blue-green color of the paint made it a good reflector of the laser light and because the paint was a thin layer on aluminum, whose high thermal conductivity would diffuse the laser-deposited heat rapidly. Curve A is an emissivity curve based on a stationary sample. Curves B and C are emissivity curves where the sample was rotated through the laser beam, at different rotational speeds with the laser at different powers. Finally, Curve D is again a reference curve based on photoacoustic absorption measurement of the sample.

Figure 6:
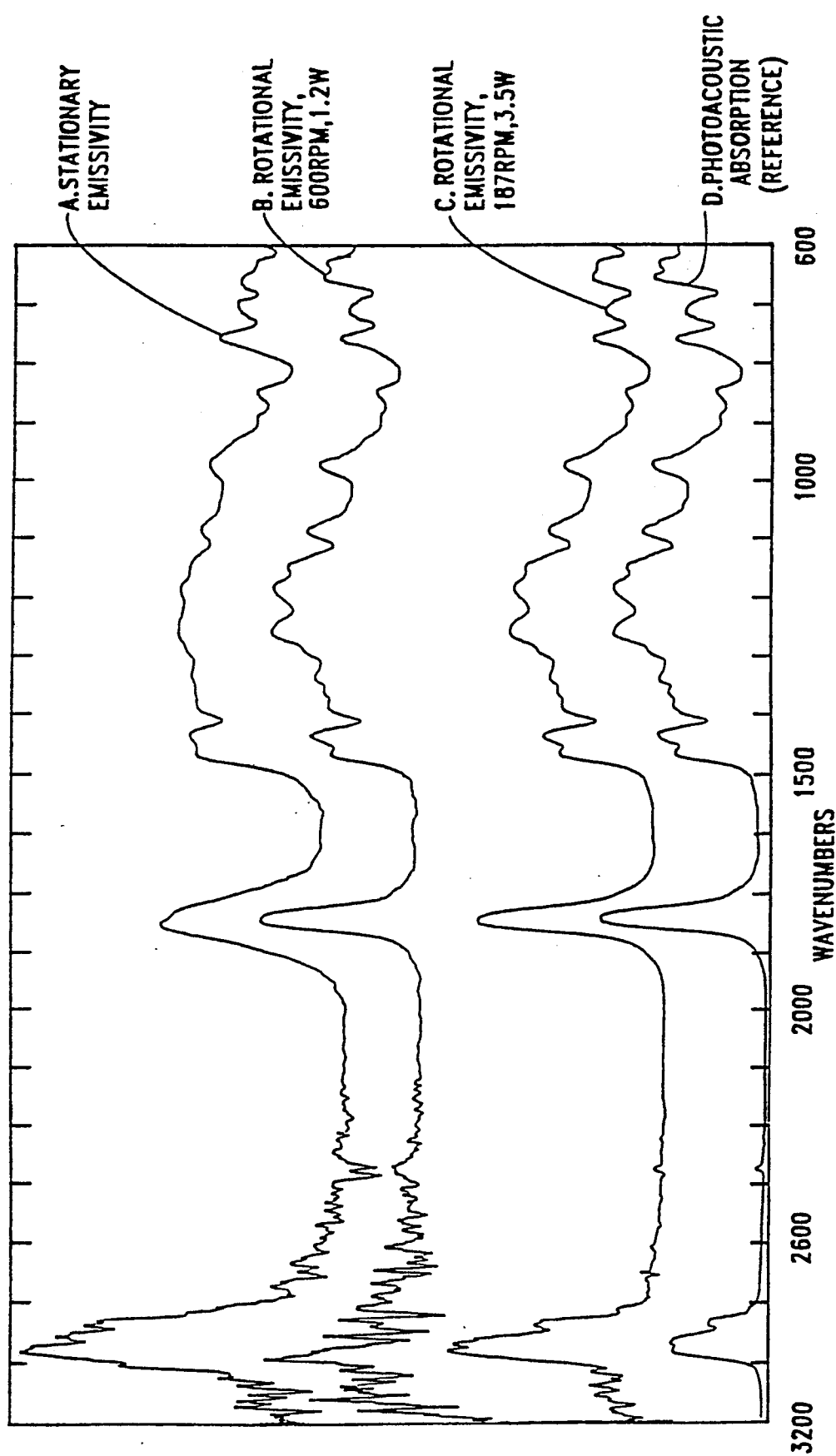
FIG. 6 is similar to FIG. 5, except it graphically depicts emissivity spectra of electrical tape.

FIG. 6 depicts the results measured according to the present invention for conventional electrical tape comprising a 0.18 mm thick (excluding adhesive), pigmented, plasticized-polyvinyl-chloride sheet. The tape was attached by its own adhesive to a 1.6 mm thick aluminum disk (44 in FIG. 2). This tape has a lower thermal-decomposition threshold than the other samples. (The maximum service temperature for plasticized polyvinyl chloride is typically 80° to 105° C.).

The spectra derived from the invention demonstrated that the invention's technique effectively reduces the saturation in the emission from optically thick samples to levels comparable to photoacoustic absorption spectra. The variety of less-than-ideal samples presented (plastic, coal, paint, electrical tape), show that the invention is potentially widely applicable and can be used on materials with high reflectivity, irregular surfaces, and moderate thermal stability. The results have good signal-to-noise ratios.

The invention provides a number of advantages over other methods. Especially important is the fact that it does not require any sample preparation, unless the composition of the surface layer probed is not related in a known way to the bulk constituents of interest. The invention is also applicable to a very wide range of situations. Depending on the analysis geometry, it can be applied to either a moving stream of material or a stationary object of any size. With a pulsed laser on a stationary target it may be possible to perform high resolution infrared microscopy of microsamples by tightly focusing the excitation beam. At the other extreme, it is possible, using a moving stream of material, to derive measurements by averaging over much more material than would be practical by conventional infrared methods. For example, with a 1 m/s material velocity, a 1 mm diameter laser spot, and a probe depth of 50 $\mu$m, a measurement by the present invention can potentially examine in an hour the same amount of material as approximately $2 \times 10^6$ KBr-pellet infrared transmission analyses, assuming the spectrometer acquires spectra at every instant. Furthermore, the actual volume of sample diluted in a pellet is assumed to be $8 \times 10^{-5}$ cm$^3$ ($10^{-4}$ cm thick and 10 mm diameter), which would produce saturation-free transmission spectra. If pellets were made that produced spectra with roughly as much saturation as the spectra discussed with regard to examples herein, each pellet could contain ten to a hundred times more sample.

The included preferred embodiments are given by way of example only, and not by way of limitation to the invention, which is solely described by the claims herein. Variations obvious to one skilled in the art will be included within the invention defined by the claims.

For example, it is to be understood that the present invention is applicable to on-line analysis of other compounds having bands in different spectral regions. It additionally is applicable to analysis of a wide range of solid materials under both moving (e.g., remote on-line) and stationary sampling conditions. Also, different types of energy sources can be substituted for a laser, if they meet the required criterion to produce the infrared emissions.

It is also to be understood that the present invention could be applied in scanned image IR microscopy. Using this process, chemical compound concentrations can be imaged at higher resolution because a shorter wavelength focus beam can be used to excite a response at longer wavelength. This can be extremely advantageous in the infrared spectra where diffraction limitations prevent high spatial resolution in conventional microscopy.

The type of instrumentation used can be tailored to meet the specific measurement requirements. A spectrometer based on a number of filters and detectors which operate simultaneously can collect spectral data 100% of the time from a flowing stream of material. An FTIR spectrometer, on the other hand, can provide much more detailed spectral information but does not collect data at every instant. Details of the excitation method can also be selected to match the particular situation. If a laser is used, laser type (pulse vs. continuous), wavelength, power, beam size, and optical geometry can all be adjusted to produce the optimum result, and yet a single set of choices can have broad applicability. Likewise the field of view of the spectrometer/detector and/or the times of detection can be controlled or selected. The examples reported herein successfully examined several disparate materials, yet were all done with a single laser, a single beam size, and a single optical geometry.

It is also to be understood that the invention can be used with factor-analysis computer software to predict a wide variety of physical and chemical material properties from infrared spectra obtained by the invention.

Additionally, it is to be understood that the present invention can be used to measure infrared spectra of discrete microsamples or of microscopic areas of larger samples in a stationary scanned imaging mode by focusing the energy beam used for heating to a small spot size. Higher resolution can be obtained using this process because the diffraction limit associated with infrared wavelengths can be avoided.

It is further to be understood that the present invention allows adjustment of the sampling depth from which spectra and hence information is obtained from a material by either changing the relative velocity between the sample and heating source or by changing the relative positioning of the heating source and the spectrometer/detector field of view or by changing the detection window times of the detector to achieve different sampling depths. For example, assuming a two layered sample, if the energy source applied heat energy to the surface of the sample directly within the spectrometer/detector field of view as discussed above, then the transient thermal emission of infrared radiation will come from only the upper layer of the sample so that the upper layer can be analyzed substantially free from any interference from the material of the underlying layer or base. If the energy source is then moved upstream on the sample flow so that the field of view of the spectrometer/detector then views a portion of the material a longer distance from the heating point, then the observed transient thermal emission of infrared radiation comes from both the upper layer, which has been previously detected and which is an optically thin upper layer, and the lower or base material layer, and such combined emissions are detected. Since the thickness of the heated lower layer or base material is greater than the thickness of the optically thin heated upper layer, the spectrum of the lower layer or base material may dominate in the combined spectrum. However, by subtracting the spectrum detected at the first position from the combined spectrum detected at the second position, a spectrum indicative of the spectrum of the lower layer or base material is obtained which is substantially free of interferences of the upper layer. Similar approaches may be utilized to focus on specific components in more complicated structures. Also, direct comparison of the spectra detected at the positions may be utilized to examine inhomogeneities. For example, if an additive designed to improve extrudability of a plastic can only perform properly if it tends to collect at the surface of the plastic, a direct spectral comparison can indicate whether or not the additive concentration is higher near the surface of the plastic.

Furthermore, it is to be understood that the apparatus and method of the invention can sample considerably larger volumes of material than would be practical by other methods and can provide time for altering processing system parameters by locating the measurement system of the invention a sufficient distance upstream from processing systems.

Moreover, it is to be understood that it may be possible in certain applications to selectively heat and thereby measure particular components in a material by tuning a heating laser absorption to that of a particular component.

Additionally, it is to be understood that the processor and graphics components of the invention can be those which are conventionally known to persons of skill in the art. Also appropriate software can be written to operate on the received data to derive the desired results of the invention.

It is further to be understood that the present invention can be altered to vary the sample depth that is sensed by adjusting the timing or position of the heat source and the spectrometer observation. Depth profile samples can be compiled by acquiring spectra at different timings or positionings corresponding to sensing depths of interest, and then performing spectral subtractions. Although photoacoustic methods of materials analysis can also vary the sample depth which is sensed, the present invention will provide more frequency and consequently more depth range for profiling, if a laser is used, because a laser source is more readily functional and can provide the high power necessary for high frequency measurements when utilized in the present invention. Additionally, photoacoustic methods require that the sample material be sealed in a chamber so that such methods are not applicable to moving materials.

We claim:

1. A method for enabling analysis of a solid material comprising the steps of:
   applying energy to a surface region of the solid material sufficient to cause transient heating in a thin surface layer portion of the solid material so as to enable transient thermal emission of infrared radiation from the thin surface layer portion; and
   detecting substantially only the transient thermal emission of infrared radiation from the thin surface layer portion of the solid material, the detected transient thermal emission of infrared radiation being sufficiently free of self-absorption by the solid material of emitted infrared radiation, so as to be indicative of characteristics relating to molecular composition of the solid material.

2. A method according to claim 1, further comprising the step of determining characteristics relating to the molecular composition of the solid material in accordance with the detected transient thermal emission.

3. A method according to claim 1, wherein the step of applying energy to a surface region of the solid material includes utilizing one of a laser, ion beam generator, electron beam generator, hot gas source, and hot roller to apply the energy.

4. A method according to claim 3, wherein the step of applying energy includes applying one of pulsed energy and continuous energy to the surface region of the solid material.

5. A method according to claim 1, wherein the solid material is one of a stationary material and a moving material.

6. A method according to claim 5, wherein the step of detecting includes detecting the transient thermal emission for a predetermined period of time upon application of the energy to the surface region.

7. A method according to claim 5, wherein the material is a moving material, and the step of detecting includes setting a field of view for detection, moving the material into the field of view upon application of the energy to the surface region of the material so as to enable detection of the transient thermal emission of infrared radiation from the surface layer portion, and then moving the surface layer portion transiently emitting the infrared radiation out of the field of view of detection.

8. A method according to claim 1, further comprising the step of additionally detecting a combination of the transient thermal emission of infrared radiation from both the thin surface layer portion of the solid material and an adjacent lower layer portion of the solid material.

9. A method according to claim 8, further comprising the step of determining characteristics relating to the molecular composition of the solid material in accordance with the detected transient thermal emission from the thin surface layer portion and the detected transient thermal emission from the lower layer portion of the solid material.

10. A method according to claim 9, wherein the step of determining characteristics includes at least one of comparing spectra of the detected transient thermal emissions from the thin surface layer portion and the lower layer portion and subtracting spectra indicative of the detected transient thermal emission from the surface layer portion from the spectra indicative of the detected combination of the transient thermal emission from the thin surface layer portion and the lower layer portion.

11. A method according to claim 1, wherein the step of detecting the transient thermal emission includes utilizing spectrometer means for detecting.

12. A method according to claim 11, wherein the spectrometer means includes filter means for filtering out at least one predetermined wavelength.

13. A method according to claim 11, further comprising the step of determining characteristics relating to the molecular composition of the solid material in accordance with the detected transient thermal emission by utilizing processing means coupled to the spectrometer means for processing the detected transient thermal emission.

14. A method according to claim 13, wherein the processing means provides an output indicative of the characteristics relating to the molecular composition of the solid material, and further comprising the step of displaying the output of the processing means.

15. A method according to claim 13, further comprising the steps of controlling at least one of the applying of energy to the surface region and the detecting of the transient thermal emission by the processing means.

16. A method according to claim 1, wherein the step of applying energy to the surface region of the solid material includes applying energy sufficiently to cause transient heating in a thin surface layer portion of the solid material without altering the solid material other than the temperature thereof.

17. An apparatus for enabling analysis of a solid material comprising:
   means for applying energy to a surface region of the solid material sufficient to cause transient heating in a thin surface layer portion of the solid material so as to enable transient thermal emission of infrared radiation from the thin surface layer portion; and
   means for detecting substantially only the transient thermal emission of infrared radiation from the thin surface layer portion of the solid material, the detected transient thermal emission of infrared radiation being sufficiently free of self-absorption by the solid material of emitted infrared radiation, so as to be indicative of characteristics relating to molecular composition of the solid material.

18. An apparatus according to claim 17, further comprising means for determining characteristics relating to the molecular composition of the solid material in accordance with the detected transient thermal emission.

19. An apparatus according to claim 17, wherein the means for applying energy to a surface region of the solid material includes one of a laser, ion beam generator, electron beam generator, hot gas source, and hot roller.

20. An apparatus according to claim 19, wherein the applying energy means includes means for applying pulsed energy and continuous energy to the surface region of the solid material.

21. An apparatus according to claim 17, wherein the detecting means include means for detecting the transient thermal emission for a predetermined period of time upon application of the energy to the surface region.

22. An apparatus according to claim 17, further comprising means for moving the solid material.

23. An apparatus according to claim 21, wherein the detecting means includes means for setting a field of view for detection, the moving means moving the material into the field of view upon application of the energy to the surface region of the material by the applying energy means so as to enable detection of the transient thermal emission of infrared radiation from the surface layer portion, the moving means thereafter moving the surface layer portion transiently emitting the infrared radiation out of the field of view of detection of the detecting means.

24. An apparatus according to claim 17, further comprising controlling means for controlling at least one of the applying energy means and the detecting means.

25. An apparatus according to claim 24, further comprising means for moving the solid material, the controlling means controlling the moving means.

26. An apparatus according to claim 24, wherein the controlling means includes processing means for determining characteristics relating to the molecular composition of the solid material in accordance with an output of the detecting means and for providing an output indicative thereof.

27. An apparatus according to claim 26, further comprising display means for displaying the output of the processing means.

28. A method for enabling analysis of a solid material comprising the steps of:

transiently generating a temperature differential between a thin surface layer portion of the solid material and a lower portion of the solid material sufficient to alter the thermal infrared emission spectrum of the solid material from the black-body thermal infrared emission spectrum of the solid material; and detecting the altered thermal infrared emission spectrum of the solid material while the altered thermal infrared emission spectrum is sufficiently free of self-absorption by the solid material of emitted infrared radiation, prior to the temperature differential propagating into the lower portion of the solid material to an extent such that the altered thermal infrared emission spectrum is no longer sufficiently free of self-absorption by the solid material of emitted infrared radiation, so that the detected altered thermal infrared emission spectrum is indicative of characteristics relating to molecular composition of the solid material.

29. A method according to claim 28, wherein the step of transiently generating a temperature differential includes applying energy to a surface region of the solid material sufficient to cause transient heating in the thin surface layer portion of the solid material so as to enable transient thermal emission of infrared radiation from the thin surface layer portion, and the step of detecting the altered thermal infrared emission spectrum of the solid material includes detecting substantially only the transient thermal emission of infrared radiation from the thin surface layer portion of the solid material, the detected transient thermal emission of infrared radiation being substantially free of self-absorption by the solid material of emitted infrared radiation.

30. A method according to claim 29, wherein the step of applying energy to a surface region of the solid material includes utilizing one of a laser, ion beam generator, electron beam generator, hot gas source and hot roller to apply the energy, and wherein the solid material is one of a stationary material and a moving material.

31. An apparatus for enabling analysis of a solid material comprising:

means for transiently generating a temperature differential between a thin surface layer portion of the solid material and a lower portion of a solid material sufficient to alter the thermal infrared emission spectrum of the solid material from the black-body thermal infrared emission spectrum of the solid material; and means for detecting the altered thermal infrared emission spectrum of the solid material while the altered thermal infrared emission spectrum is sufficiently free of self-absorption by the solid material of emitted infrared radiation, prior to the temperature differential propagating into the lower portion of the solid material to an extent such that the altered thermal infrared emission spectrum is no longer sufficiently free of self-absorption by the solid material of emitted infrared radiation, so that the detected altered thermal infrared emission spectrum is indicative of characteristics relating to molecular composition of the solid material.

32. An apparatus according to claim 31, wherein the means for transiently generating a temperature differential includes means for applying energy to a surface region of the solid material sufficient to cause transient heating in the thin surface layer portion of the solid material so as to enable transient thermal emission of infrared radiation from the thin surface layer portion, and the means for detecting the altered thermal infrared emission spectrum of the solid material includes means for detecting substantially only the transient thermal emission of infrared radiation from the thin surface layer portion of the solid material, the detected transient thermal emission of infrared radiation being sufficiently free of self-absorption by the solid material of emitted infrared radiation.

33. An apparatus according to claim 32, wherein the means for applying energy to a surface region of the solid material includes one of a laser, ion beam generator, electron beam generator, hot gas source, and hot roller.

34. An apparatus according to claim 33, further comprising means for moving the solid material.

* * * * *

UNITED STATES PATENT AND TRADEMARK OFFICE
CERTIFICATE OF CORRECTION

PATENT NO.    : 5,075,552           Page 1 of 1
DATED         : December 24, 1991
INVENTOR(S)   : McClelland et al.

It is certified that error appears in the above-identified patent and that said Letters Patent is hereby corrected as shown below:

Column 1,
Line 5, insert
-- STATEMENT REGARDING FEDERALLY SPONSORED RESEARCH AND DEVELOPMENT
This invention was made in part with Government support under the United States Department of Energy Contract No. W-7405-Eng-82. The Government may have certain rights in this invention. --

Signed and Sealed this

Twenty-sixth Day of August, 2003

JAMES E. ROGAN
*Director of the United States Patent and Trademark Office*